US008175695B2

(12) United States Patent
Rouw et al.

(10) Patent No.: US 8,175,695 B2
(45) Date of Patent: May 8, 2012

(54) T-WAVE ALTERNANS TRAIN SPOTTER

(75) Inventors: Mattias Rouw, Arnhem (NL);
Christianus J. J. E. Van Groeningen, Utrecht (NL); Henricus Willem M. De Bruyn, Arnhem (NL)

(73) Assignee: Medtronic, Inc., Minneapolis, MN (US)

( * ) Notice: Subject to any disclaimer, the term of this patent is extended or adjusted under 35 U.S.C. 154(b) by 1 day.

(21) Appl. No.: 12/708,080

(22) Filed: Feb. 18, 2010

(65) Prior Publication Data
US 2010/0145404 A1 Jun. 10, 2010

Related U.S. Application Data

(62) Division of application No. 10/755,694, filed on Jan. 12, 2004, now Pat. No. 7,725,174.

(51) Int. Cl.
*A61B 5/0452* (2006.01)
*A61B 5/0468* (2006.01)
(52) U.S. Cl. ............................ 600/516; 600/509
(58) Field of Classification Search .................. 600/509, 600/516
See application file for complete search history.

(56) References Cited

U.S. PATENT DOCUMENTS

| | | | |
|---|---|---|---|
| 4,316,472 A | 2/1982 | Mirowski et al. | |
| 4,375,817 A | 3/1983 | Engle et al. | |
| 4,379,459 A | 4/1983 | Stein | |
| 4,384,585 A | 5/1983 | Zipes | |
| 4,476,868 A | 10/1984 | Thompson | |
| 4,566,063 A | 1/1986 | Zolnowsky et al. | |
| 4,577,633 A | 3/1986 | Berkovits et al. | |
| 4,587,970 A | 5/1986 | Holley et al. | |
| 4,726,380 A | 2/1988 | Vollmann et al. | |
| 4,727,877 A | 3/1988 | Kallok | |
| 4,800,883 A | 1/1989 | Winstrom | |
| 4,802,491 A | 2/1989 | Cohen et al. | |
| 4,821,723 A | 4/1989 | Baker et al. | |
| 4,830,006 A | 5/1989 | Haluska et al. | |
| 4,880,005 A | 11/1989 | Pless et al. | |
| 4,949,719 A | 8/1990 | Pless et al. | |
| 4,953,551 A | 9/1990 | Mehra et al. | |

(Continued)

FOREIGN PATENT DOCUMENTS

WO    WO 92/18198 A2    10/1992

(Continued)

OTHER PUBLICATIONS

U.S. Appl. No. 09/558,871, filed Apr. 28, 2000, "Implantable Medical Device and Method Using Integrated T-Wave Alternans Analyzer".

(Continued)

*Primary Examiner* — Tammie K Heller
(74) *Attorney, Agent, or Firm* — Reed A. Duthler

(57) ABSTRACT

A method and system for detecting T-wave alternans for use in an implanted medical device uses wave transformation of QT intervals to obtain a reliable measure of TWA. In one embodiment, an array provides alternating sign multiplication factors which are applied respectively to n consecutive QT values. Each successive QT value is high pass filtered and moved sequentially through a queue so that each cycle each of the n QT values is multiplied by one of the factors; the products are summed and made absolute to provide an alternans match value. The alternans match is compared with a noise threshold signal, and alternans is declared when the match exceeds the threshold by a predetermined amount. The array is programmable and can be varied, providing a high degree of flexibility to optimize the test for the patient.

8 Claims, 10 Drawing Sheets

U.S. PATENT DOCUMENTS

| | | | |
|---|---|---|---|
| 5,099,838 | A | 3/1992 | Bardy |
| 5,117,824 | A | 6/1992 | Keimel et al. |
| 5,131,388 | A | 7/1992 | Pless et al. |
| 5,144,949 | A | 9/1992 | Olson |
| 5,148,812 | A | 9/1992 | Verrier et al. |
| 5,158,078 | A | 10/1992 | Bennett et al. |
| 5,163,427 | A | 11/1992 | Keimel |
| 5,188,105 | A | 2/1993 | Keimel |
| 5,199,428 | A | 4/1993 | Obel et al. |
| 5,207,218 | A | 5/1993 | Carpentier et al. |
| 5,269,298 | A | 12/1993 | Adams et al. |
| 5,312,453 | A | 5/1994 | Shelton et al. |
| 5,314,430 | A | 5/1994 | Bardy |
| 5,330,507 | A | 7/1994 | Schwartz |
| 5,331,966 | A | 7/1994 | Bennett et al. |
| 5,354,316 | A | 10/1994 | Keimel et al. |
| 5,545,186 | A | 8/1996 | Olson et al. |
| 5,560,370 | A | 10/1996 | Verrier et al. |
| 5,690,686 | A | 11/1997 | Min et al. |
| 5,800,465 | A | 9/1998 | Thompson et al. |
| 5,842,997 | A | 12/1998 | Verrier et al. |
| 5,891,045 | A | 4/1999 | Albrecht et al. |
| 5,921,940 | A | 7/1999 | Verrier et al. |
| 6,047,206 | A | 4/2000 | Albrecht et al. |
| 6,132,381 | A | 10/2000 | Forbes et al. |
| 6,169,919 | B1 | 1/2001 | Nearing et al. |
| 6,272,377 | B1 | 8/2001 | Sweeney et al. |
| 6,983,183 | B2 | 1/2006 | Thiagarajan et al. |
| 2001/0029338 | A1 | 10/2001 | Krishnamachari |

FOREIGN PATENT DOCUMENTS

| | | | |
|---|---|---|---|
| WO | WO 01/22878 A1 | 5/2001 | |

OTHER PUBLICATIONS

Klingenheben, T., et al., "T Wave Alternans in the Microvolt Range as a New Indicator of Abnormal Ventriculra Repolarization: Pathophysiology, Methodology, and Clinical Results", *Z Kardiol*, 88:974-981 (1999) (translated into English).

Arzbaecher, R., et al., "Automatic Tachycardia Recognition", *PACE*, vol. 7, pp. 541-547, May-Jun. 1984, Part II.

Olson, W., et al., "Onset and Stability for Ventricular Tachyarrhythmia Detection in an Implantable Pacer-Cardioverter-Defibrillator", *Computers in Cardiology*, Oct. 7-10, 1986, pp. 167-170.

Klingenheben, T., et al., "Predictive Value of T-wave Alternans for Arrhythmic Events in Patients with Congestive Heart Failure", *The Lancet, Research Letters*, vol. 356, Aug. 19, 2000, pp. 651-652.

Hennersdorf, M., et al., "T Wave Alternans as a Risk Predictor in Patients with Cardiomyopathy and Mild-to-Moderate Heart Failure", *PACE*, vol. 23., Sep. 2000, pp. 1386-1391.

Houltz, B. et al., "Electrocardiographic and Clinical Predictors of Torsades de Pointes Induced by Almokalant Infusion in Patients with Chronic Atrial Fibrillation or Flutter", *PACE*, vol. 21, p. 1044-57 (May 1998).

T-WAVE ALTERNANS TRAIN SPOTTER

RELATED APPLICATION

This application is a divisional of U.S. Patent Application Ser. No. 10/755,694, filed Jan. 12, 2004 entitled "T-Wave Alternans Train Spotter", now U.S. Pat. No. 7,725,174, issued May 25, 2010, herein incorporated by reference in its entirety.

In addition, the present invention claims priority and other benefits from U.S. Provisional Patent Application Ser. No. 60/439,459, filed Jan. 13, 2003, entitled "T-WAVE ALTERNANS TRAIN SPOTTER ", incorporated herein by reference in its entirety.

FIELD OF THE INVENTION

This invention relates to cardiac devices and methods of using such devices and, more particularly, devices and methods for detecting T-wave alternans in a cardiac patient.

BACKGROUND OF THE INVENTION

It has become well known that T-wave alternans has predictive value for arrhythmic events such as tachyarrhythmias. T-wave alternans has been determined to be an indicator of various forms of disordered ventricular repolarization, including disorders found in patients with cardiomyopathy, mild to moderate heart failure, and congestive heart failure. The following literature references deal with the subject of T-wave alternans as a predictor: Klingenheben T, Siedow A, Credner S C, Gronefeld, et al., T-Wave Alternans in microwave frequency as a new indicator of disordered ventricular repolarization: pathophysiology, methodology, clinical results, Z Kardiol, 1999, Dec., 88 (12), 974-81; Klingenheben T, Zabel M, D'Agostino R B, Cohen R J et al., Predictive value of T-Wave Alternans for arrhythmic events in patients with congestive heart failure, Lancet, 2000, Aug. 19; 356 (9230): 651-2; and Hennersdorf M G, Perings C, Niebch V, Vester E G, et. al., T-Wave Alternans as a risk predictor in patients with cardiomyopathy and mild-to-moderate heart failure, Pacing Clin Electrophysiol 2000 Sep.; 23(9); 1386-91.

T-wave alternans (TWA) may be caused by changes in ion exchange during repolarization. If there is a change in the repolarization mechanism on one beat, the heart attempts to readjust on the following beat. This is manifested as an alternating change in the action potential. In the surface ECG this is seen primarily as an amplitude change. For an implanted medical device such as a cardiac pacemaker, the intracardiac electrogram (iecg) also shows a change in timing. Thus, the term T-wave as used herein may refer to a portion of the ventricular QRS-T-wave complex that includes the T-wave and the QRS-T segment. The alternating feature of TWA can be detected by examination, for example, of the QT interval, T-wave width, T-wave morphology, etc. Whatever the designated portion of the iecg, T-wave alternans refers to an alternating pattern of the wave that can be designated "A-B-A-B-A . . . " where A represents every other cycle and B represents every other alternate cycle. As discussed in the literature, when such an alternating pattern appears, the different rates or forms of repolarization of the ventricular cells are statistically associated with a variety abnormal cardiac conditions. Further, the alternating repolarization pattern can lead to increased instability and consequent cardiac arrhythmias. Thus, T-wave alternans is recognized as an indicator of risk for ventricular arrhythmia and even sudden cardiac death.

The prior art discloses several different methods and techniques for detecting T-wave alternans. TWA can be measured non-invasively by exercise-inducing an elevated heart rate in the patient and then measuring the surface ECG with special electrodes and computer analysis. Moreover, it has been disclosed that measurement of the TWA through the IECG obtained by an implanted medical device provides the capability of obtaining improved waveform data and analysis for detection of TWA. See U.S. patent application Ser. No. 09/558,871, filed Apr. 28, 2000, "Implantable Medical Device and Method Using Integrated T-Wave Alternans Analyzer", Morris et al. This patent is incorporated herein by reference in its entirety.

BRIEF DESCRIPTION OF THE DRAWINGS

Various aspects and features of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE INVENTION

The present invention provides a system and method for determining TWA in a patient, the system and method constituting an improvement over the prior art that enables a more accurate detection of TWA and more flexibility in optimizing TWA detection for the patient under examination.

In an embodiment of the present invention, an adaptable transformation program is utilized for applying an alternating sign array to a series of consecutive T-wave signals. As used in the Specification and Claims that follow, T-wave comprises not only the T-wave portion of the ventricular IECG but also the S-T segment or the Q-T interval. In the an embodiment of the invention, QT intervals are sensed each cycle, and the invention operates cyclically to provide an indication of whether or not T-wave alternans has been detected.

In an embodiment of the invention, a transformation array is in the form A-B-A, A-B-A-B, A-B-A-B-A, etc. where A is a positive factor and a B is a negative factor. Consecutive values of QT (or other portion of the sensed ventricular wave) are stored in a queue, multiplied respectively by the pattern factors, and then summed. The pattern may have an odd number of factors or an even number of factors. The pattern array may be programmable or automatically selected from a plurality of different arrays, thereby providing the user with the ability to optimize the pattern for the individual patient. After each factor of the array is multiplied by the corresponding respective QT interval from the series of QT intervals being examined, the products are summed and then preferably squared to get an absolute value. This absolute value, referred to as the alternans match, is compared to a noise threshold that is representative of the noise level in the QT sensor. When the alternans match exceeds threshold, alternans is deemed to have been determined.

In another embodiment of the invention the QT signals are high pass filtered before undergoing transformation, removing the steady state value of each AT interval so that the transformation is done on plus and minus differential values. The filtering function may be undertaken by hardware such as is available from a DSP chip. Alternately, the high pass filter function may be incorporated into the pattern, so that the transformation operation on each series of QT intervals incorporates the high pass filtering step. This makes implementation of the method simpler and requires less computing resources, which is of course advantageous for an implanted device.

In the system of this invention the result of each T-wave alternans analysis is suitably stored in memory for later interrogation and retrieval. Further, for each T-wave alternans test, the pattern used (e.g., the number of factors and the value of each of the factors of the pattern) can be stored, so that a determination can be made as to the optimum pattern for the patient.

Figure 1:
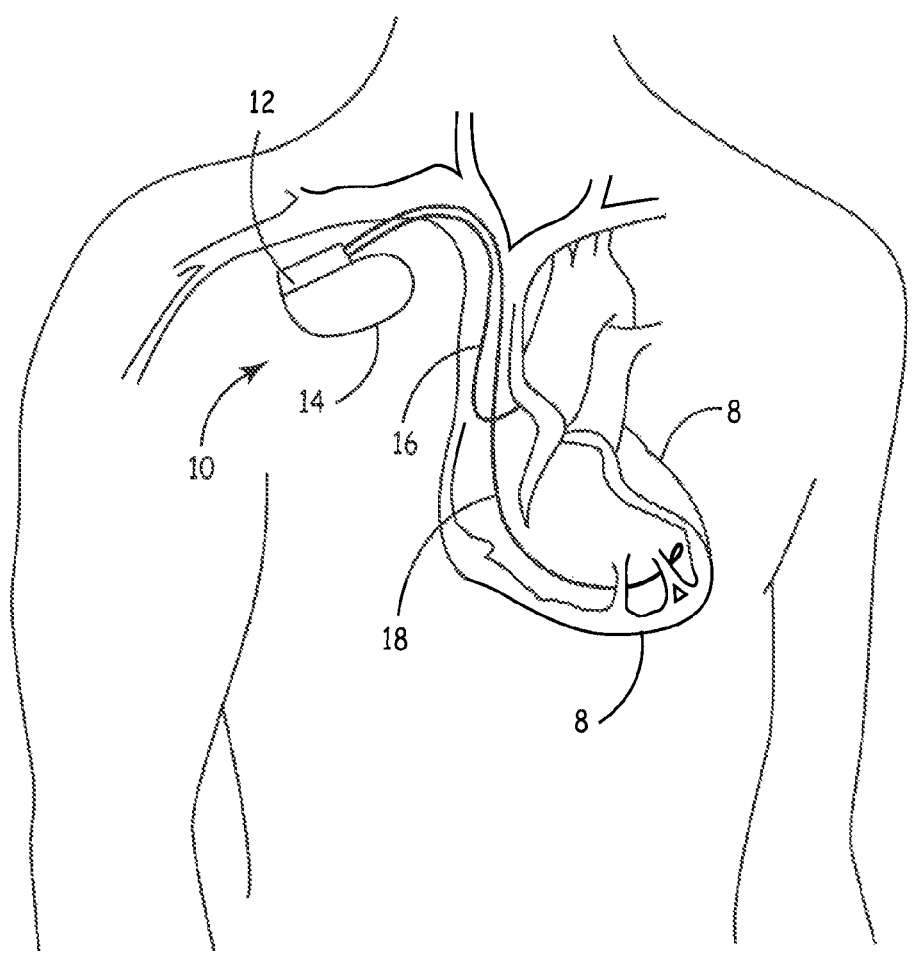
FIG. 1 is a simplified schematic view of one embodiment of an implantable medical device that can be employed in the present invention.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
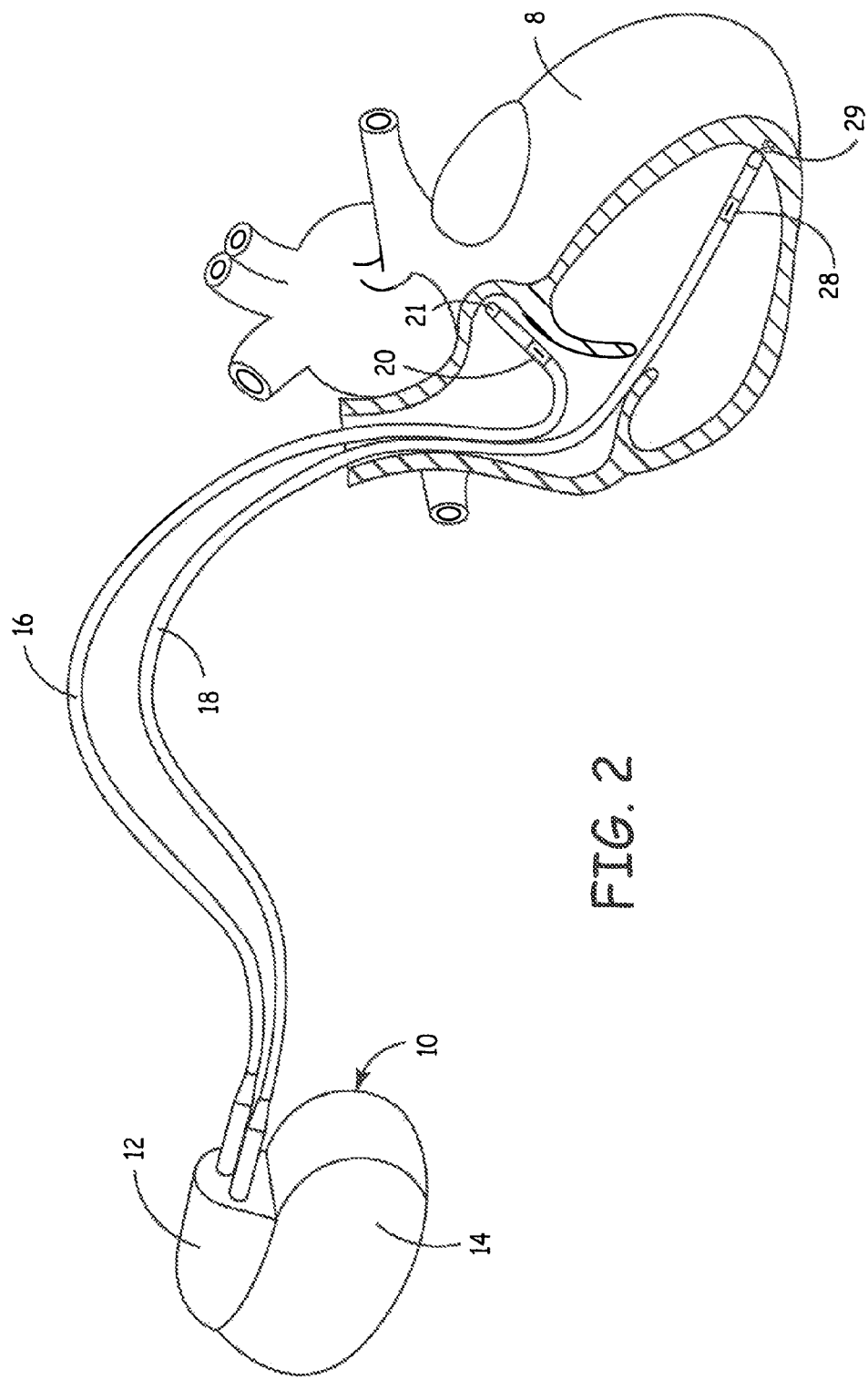
FIG. 2 is a graphic representation of an implantable medical device interconnected with a human or mammalian heart, illustrating the device connecter portion and the leads between the device and the heart.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
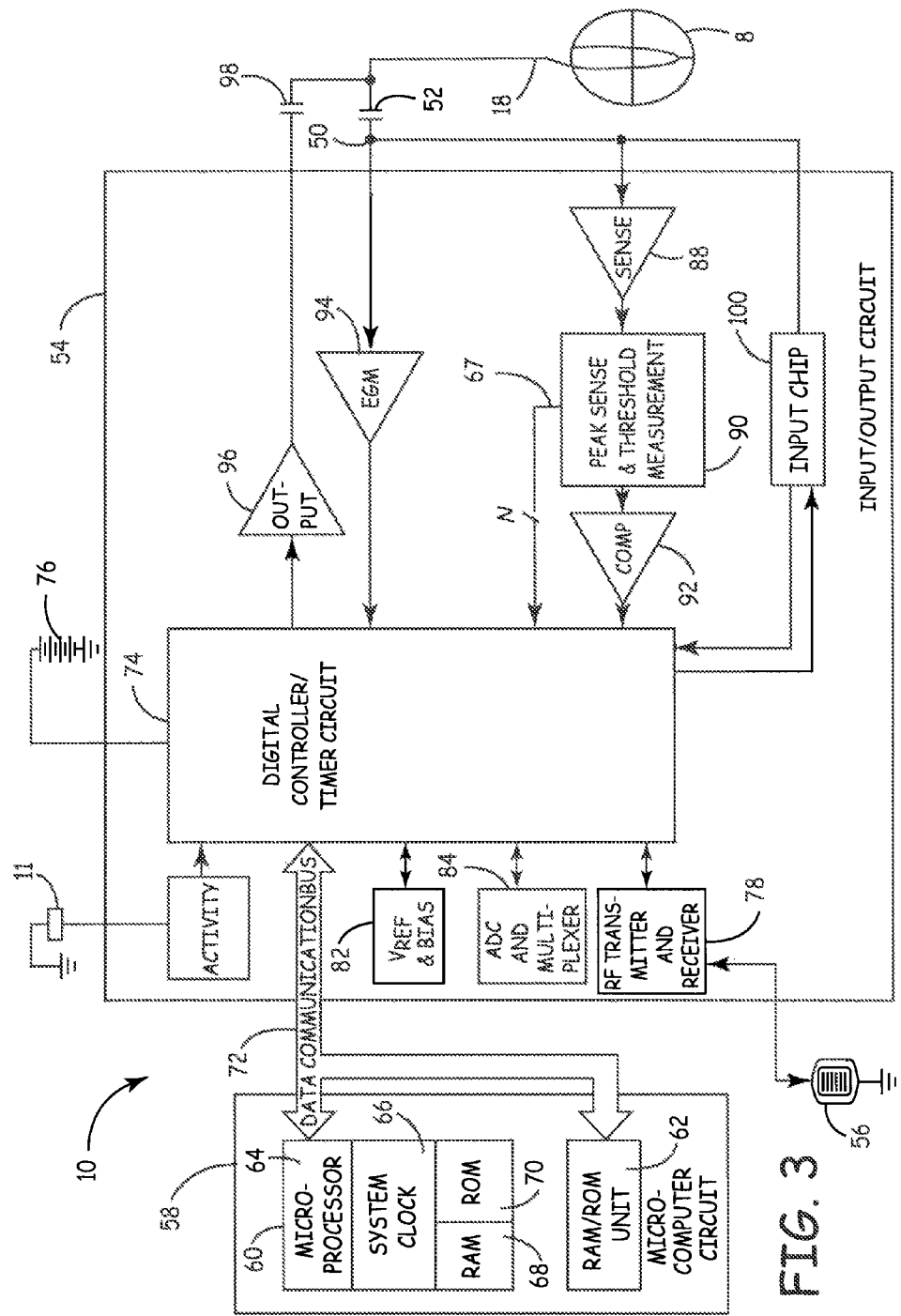
FIG. 3 is a functional schematic diagram showing the primary constituent components of an implantable medical device in accordance with an embodiment of this invention.

FIG. 3 shows a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored in microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. According to an embodiment of the invention, the particular programming and telemetry scheme are selected to permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety. The functions performed by elements 88,90,92 may alternately be performed by an input DSP chip as shown at 100; the DSP chip may also perform other functions such as high pass filtering and array transformation, as discussed below in detail.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some embodiments of the present invention, IMD 10 may operate in various non-rate-responsive modes, including, but not limited to, DDD, DDI, VVI, VOO and VVT modes. In other embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 4:
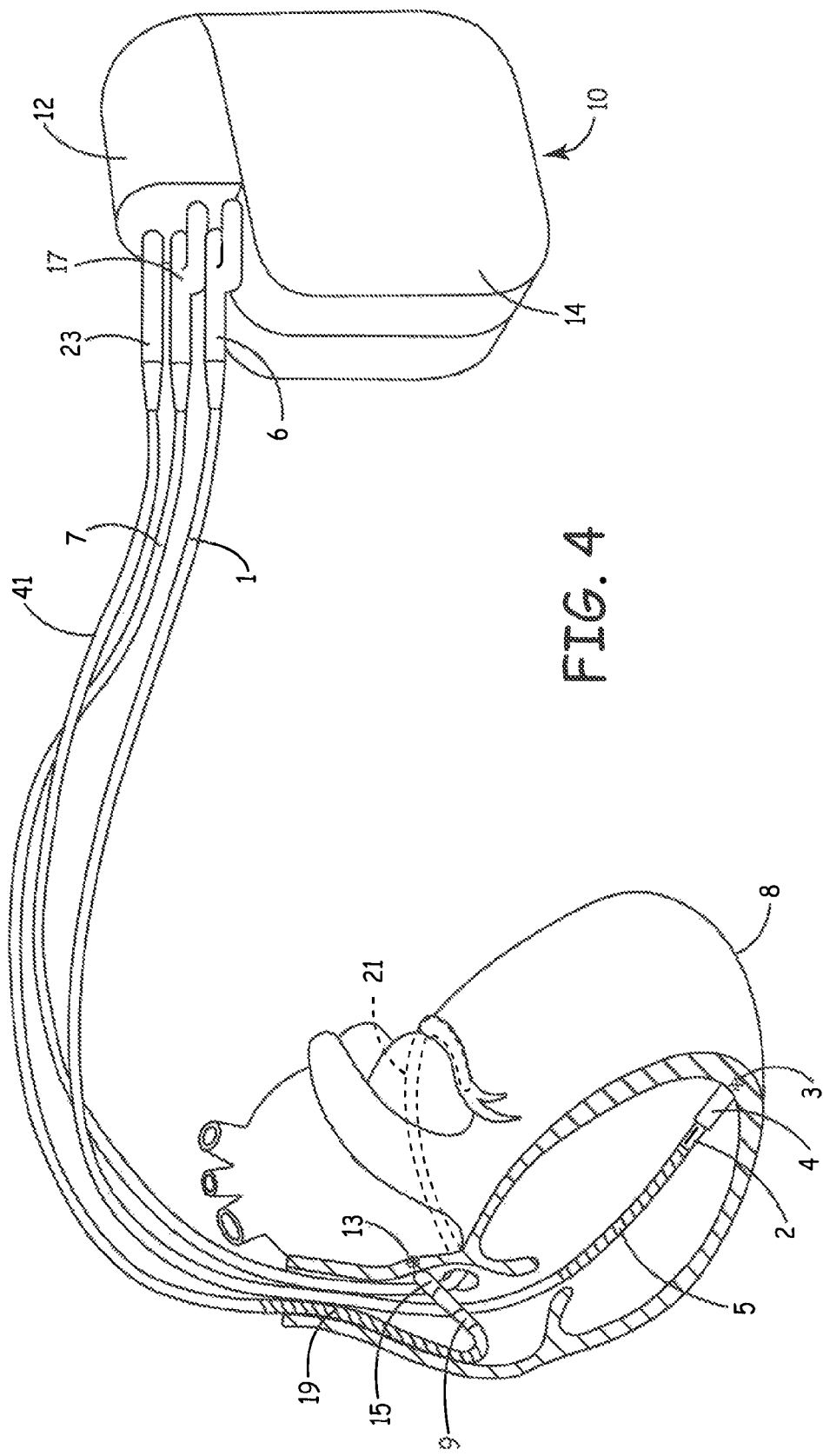
FIG. 4 is a graphic representation of an embodiment of this invention showing an implantable PCD device interconnected with the heart, the system of this embodiment providing pacing, cardioversion and defibrillation.
Figure 5:
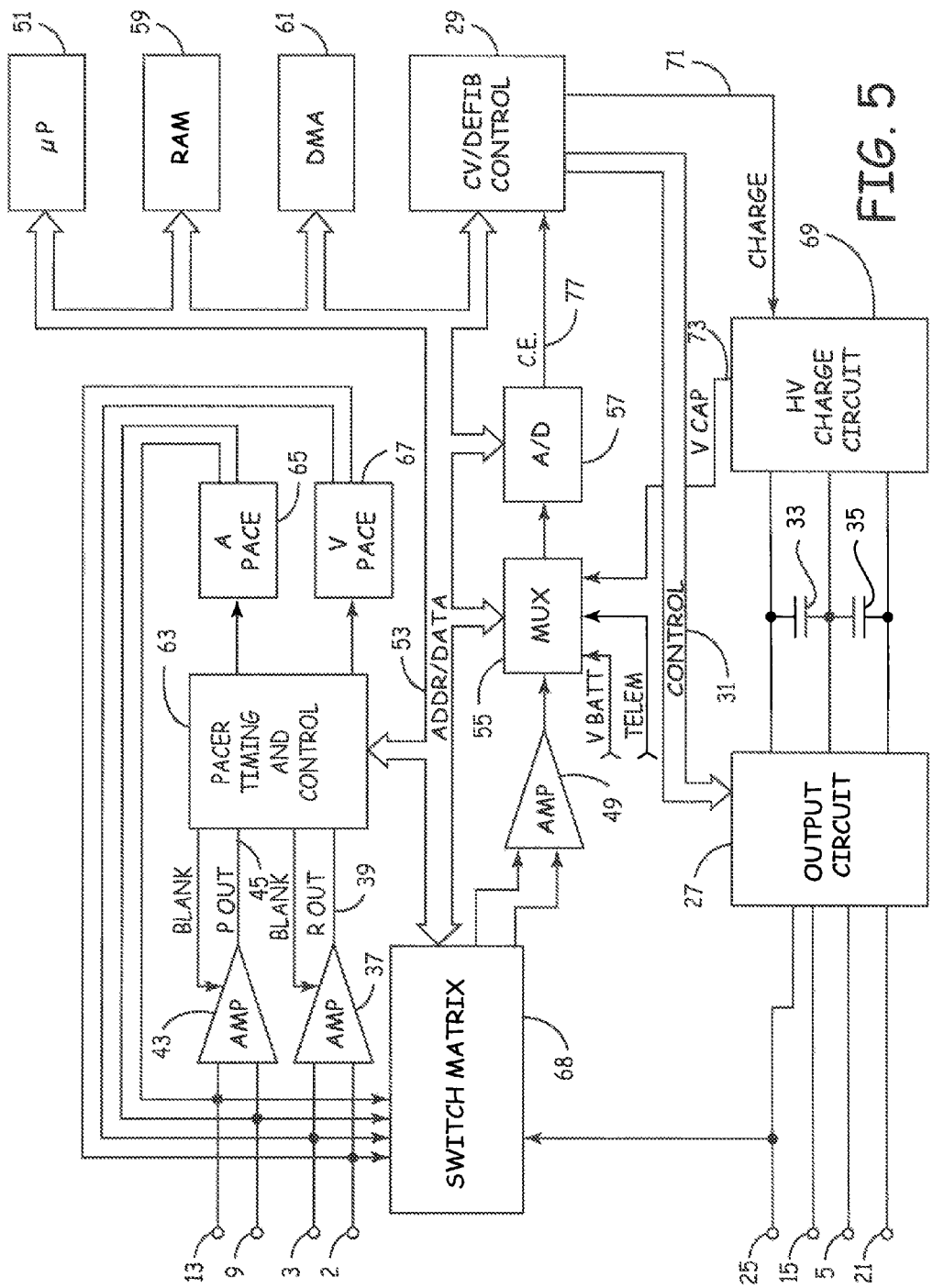
FIG. 5 is a functional schematic diagram of an implantable PCD embodiment in accord with this invention.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5-200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by ND converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7-10, 1986, IEEE Computer Society Press, pages 167-170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May-June, 1984, pp. 541-547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to a cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Figure 6:
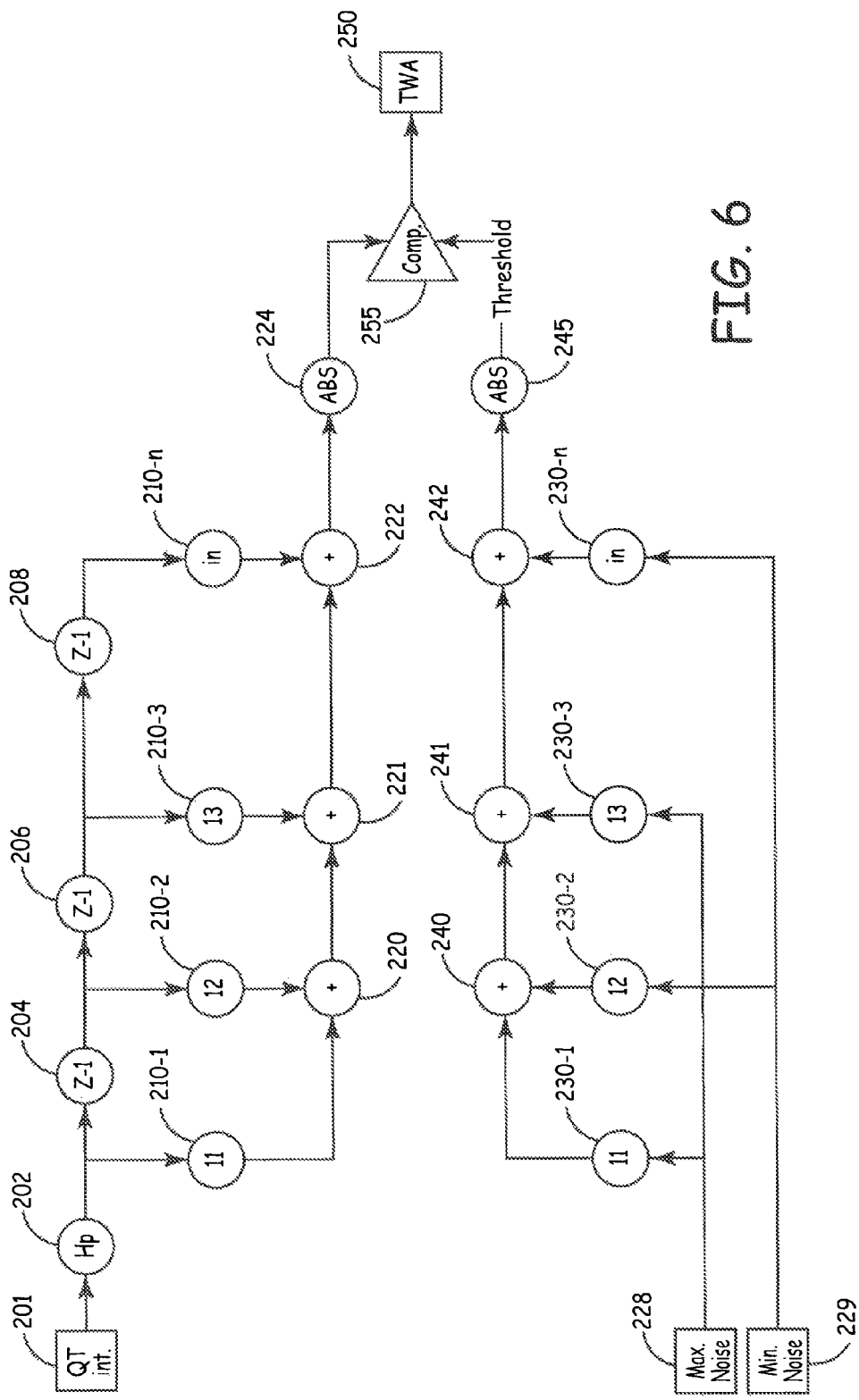
FIG. 6 is a schematic wavelet transformation diagram for determining T-Wave ALternans in accordance with this invention.
Figure 7:
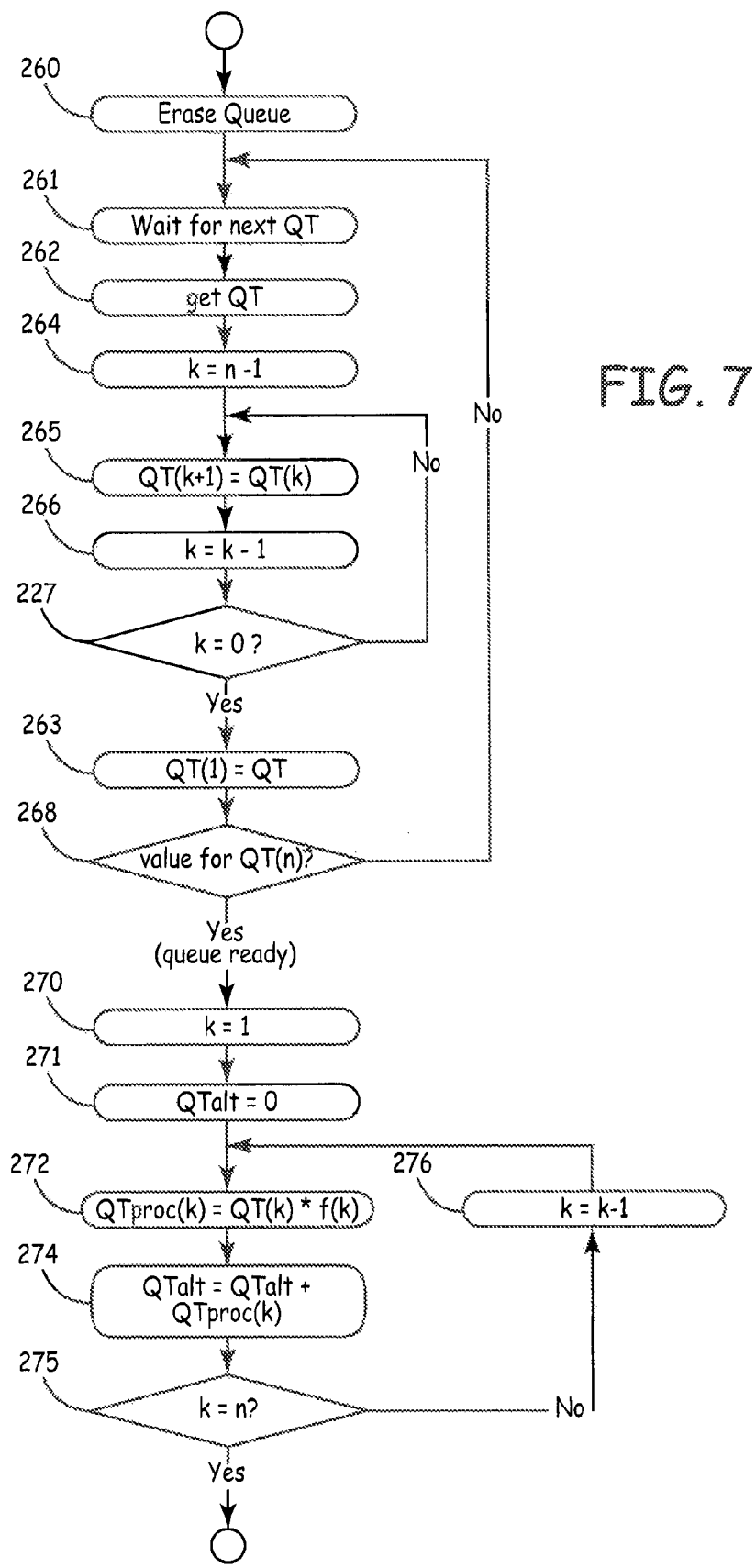
FIG. 7 is a flow diagram illustrating the steps taken in carrying out the wavelet transformation of FIG. 6.

FIG. 6 is a schematic diagram of the pattern array transformation according to an embodiment of this invention. The illustrated steps can be executed by software in the microprocessor, as illustrated in FIG. 7, or can be executed by the dedicated hardware such as a DSP circuit (chip 100 in FIG. 3) assigned to this task. As used herein, the terms circuit and program are both used to describe the architecture for carrying out the steps illustrated in FIGS. 6 and 7.

The specific improvements of the invention are illustrated by reference to FIGS. 6-10. At the beginning of the test, shown at 201 of FIG. 6, the QT interval is detected. Each successive QT interval during alternans train detecting is passed through a high pass filter as shown at 202, in order to remove low frequency components to the QT signal. Thus, the high pass filter effectively removes the average value of QT and provides at its output a QT interval change, either plus or minus around the average value. This is illustrated in the bottom curve of FIG. 8, which shows a plot of typical QT values after having passed through the high pass filter. Each filtered QT interval signal is passed into a delay queue, comprising n−1 delay elements 204,206-208. The nomenclature Z−1 indicates a delay of one sample interval cycle, i.e., a delay of one R-R interval. Each just detected filtered QT interval signal is connected to a multiplier element 210-1, shown as f1, while each previous sample is connected to a queue position related multiplier element (210-2 ... 210-n). As seen in FIG. 6, f1 ... fn are the multiplier factors, and may be for example, 1, minus 1, 1, minus 1, .... Thus for the current transformation, the just detected QT interval is multiplied by f1; the previous sample by f2; and the last sample in the queue by fn−1. For each transformation operation the outputs of the multiplier elements f1-fn are added by adder elements 220, 221 ... 222, to provide a transformation output. This output, which may be signed plus or minus, is processed through absolute element 224, which suitably squares the sum of the total to provide an output having an absolute value. This in turn is inputted to a comparator 225, and compared to a noise threshold signal to determine whether or not there is TWA. The result of the comparison is handled at block 250, and gives an output when there is TWA.

Figure 8:
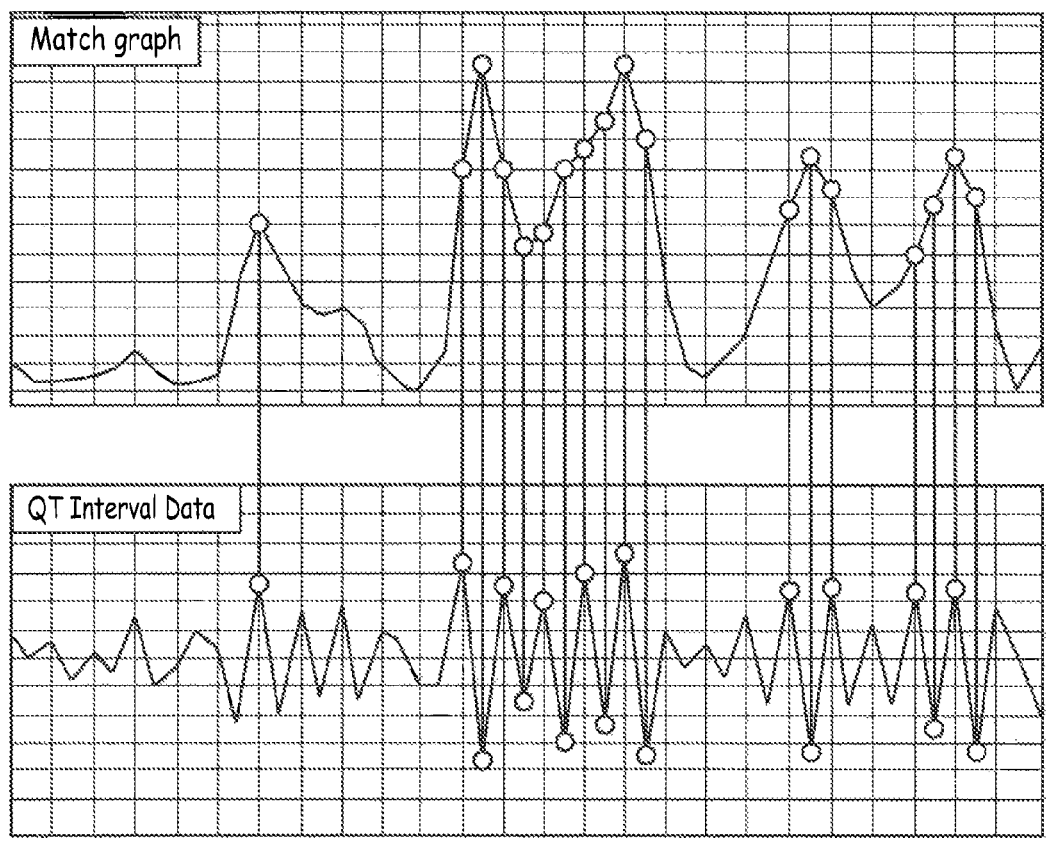
FIG. 8 shows a comparison of QT interval data and alternans match data, representing the practice of this invention.

FIG. 8 shows a representative match in the upper graph, corresponding to the filtered QT interval data shown in the bottom graph. Examination of the QT interval graph shows that high pass variations from beat to beat are relatively small, and in this example are between plus and minus two ms. In any given case, variations may be larger, but could be within only several ms. Given this knowledge, it is important to take into account the noise level on the V-sense channel, in order to determine whether the alternans match is a valid representation of TWA or is in fact a product primarily of noise. For this reason a noise threshold signal is developed as seen in the lower branch of FIG. 6. At 228 a maximum noise level, e.g., 0-2 ms in inputted, and at 229 a minimum noise level in the same range is inputted. These are default values that are pre-determined based on sample accuracy and normal variations. In the illustration of FIG. 8 the swings of QT interval data (representing different values from beat to beat, after the high pass filtering) are seen to be in the range of about 0.5 to 2.0. For this example, the maximum noise value may be set, e.g., at 1.0 ms. and the minimum noise value may be set, e.g., at −1.0 ms. The max and min noise values are operated on by the respectively odd and even elements in an array of n multiplier factors, shown at 230-1 through 230-n. The multiplied values are summed at adding elements shown at 240, 241 ... 242, and then made absolute as shown at element 245. The operation at elements 224 and 245 are the same and suitably may simply involve squaring the summation values presented to each. The output from 245 is inputted to comparator 225 as a noise threshold value. In one embodiment of the invention, if the output of the operation at 224 exceeds the threshold value from 245, a signal is passed to TWA analysis element 250, where TWA is declared. It is to be understood that other steps may be added to the determination of TWA. For example, TWA can be declared only after the alternans match from element 225 exceeds the noise threshold from 245 for x consecutive cycles, or for some fraction of cycles. Further, a constant can be added to the output of element 245, to ensure that the alternans match is sufficiently above noise to guarantee declaration of TWA.

Inspection of FIG. 8 shows the operation by which alternans match values, generated by the step shown at 224, relate to QT interval data. As is seen, the high pass filtered QT interval data varies above and below the zero reference line, representing an alternating QT interval. The match graph represents data taken from a one, minus one, one array (also represented as [1,−1,1] with the match value corresponding to the center QT measurement. In this actual example of patient data, the noise detection threshold is ten, and the alternans is spotted above this level as indicated at the circled dots. Each match figure corresponds to the center QT interval, i.e., the match represents the transformation obtained by operating on the current QT interval, the prior QT interval and the next following QT interval. For example, the first match that is circled indicates an alternans match having a value of about 12.25. This was obtained by operating on QT values of minus 1.2, plus 1.4, and minus 0.9. When these values were multiplied and summed by the array [1,−1, 1] this yields 3.5. The value of 3.5 squared equals 12.25.

As illustrated in FIG. 6, high pass filtering is done prior to the transformation. Further advantage can be obtained by eliminating the filtering as a separate step and incorporating it into the transformation, which makes the implementation easier and reduces the computer or processor requirements. A high pass filtering function is obtained by operating on the array for the previous sample by minus 1 and the array for the current sample by plus 1. Adding these two operations together, an array, or template [−1,+2,−1] is changed to [−1, 3,−3,1]. Thus, an n factor array for use with the high pass filtered signal is replaced by an n+1 array for an unfiltered signal. The changed array accentuates the differences from beat to beat so as to provide the high pass filter function. Thus, instead of the operation shown if FIG. 6 of first high pass filtering the QT interval, the high pass filter operation shown at 202 is eliminated and the n array is changed to incorporate the high pass filtering function. In the latter case, all the inputted QT values are of the same sign and accordingly for an array or template having an odd number of factors, the A-B-A-B-A pattern is changed to the following: 1, 1+1/n, −1, 1+1/n, −1 ...

The transformation array of FIG. 6 can be embodied by hardware or software. Implementation in either form is within the ordinary skill of one in the art area. A hardware embodiment suitably incorporates a DSP chip under command of the microprocessor. The delay functions are accomplished by cyclically clocking each value of QT to a next location in a software queue, following which the multiplication and addition functions are carried out.

A software embodiment of the array transformation is illustrated in FIG. 7. At the start of a new test the queue is erased, as shown at 260. At 261 the device waits for the next QT, and at 262 a new QT is received. At 264 a factor k is set to n−1, where n is the number of factors in the array. At 265 QTk+1=QTk, meaning that the kth value of QT is advanced to the next position, corresponding to a delay function illustrated in FIG. 6 by a "Z−1" element. Next, at 266, k is set=k−1. At 267 a check is made to see if k=0, which would mean that all previously stored QT values have been advanced in the queue. If not, the programs loops back to 265 and repeats until k=0. When all the previously stored QT values are advanced, at 263 the new QT is designated QT1. At that time, the program checks to see that there is indeed a value for QTn, meaning the queue is full. If not, as happens when a test first starts and it takes n cycles to fill the queue, the program returns to 261 and waits for the next QT. When a value of QTn is found at 268, the queue is ready and the program proceeds to carry out the multiplication and addition functions as shown at 272, 274, 275 and 276. When these have been completed, as determined at 275, the array transformation is complete and the QT alternans value QTalt is obtained. The program then goes on to the step of making QTalt absolute, and comparing with the noise threshold. The steps for generating the noise threshold are straightforward multiplication and addition steps, as illustrated in FIG. 6. Of course, the noise threshold need be calculated only once for each test; but whenever the array is changed, i.e., n is changed, then the noise threshold must again be calculated.

As noted above, the terms "program" and "circuit" are used in the claims to denote either a hardware or software embodiment. Thus, a circuit or circuitry can be, e.g., DSP circuitry or a programmed microprocessor system.

Figure 9:
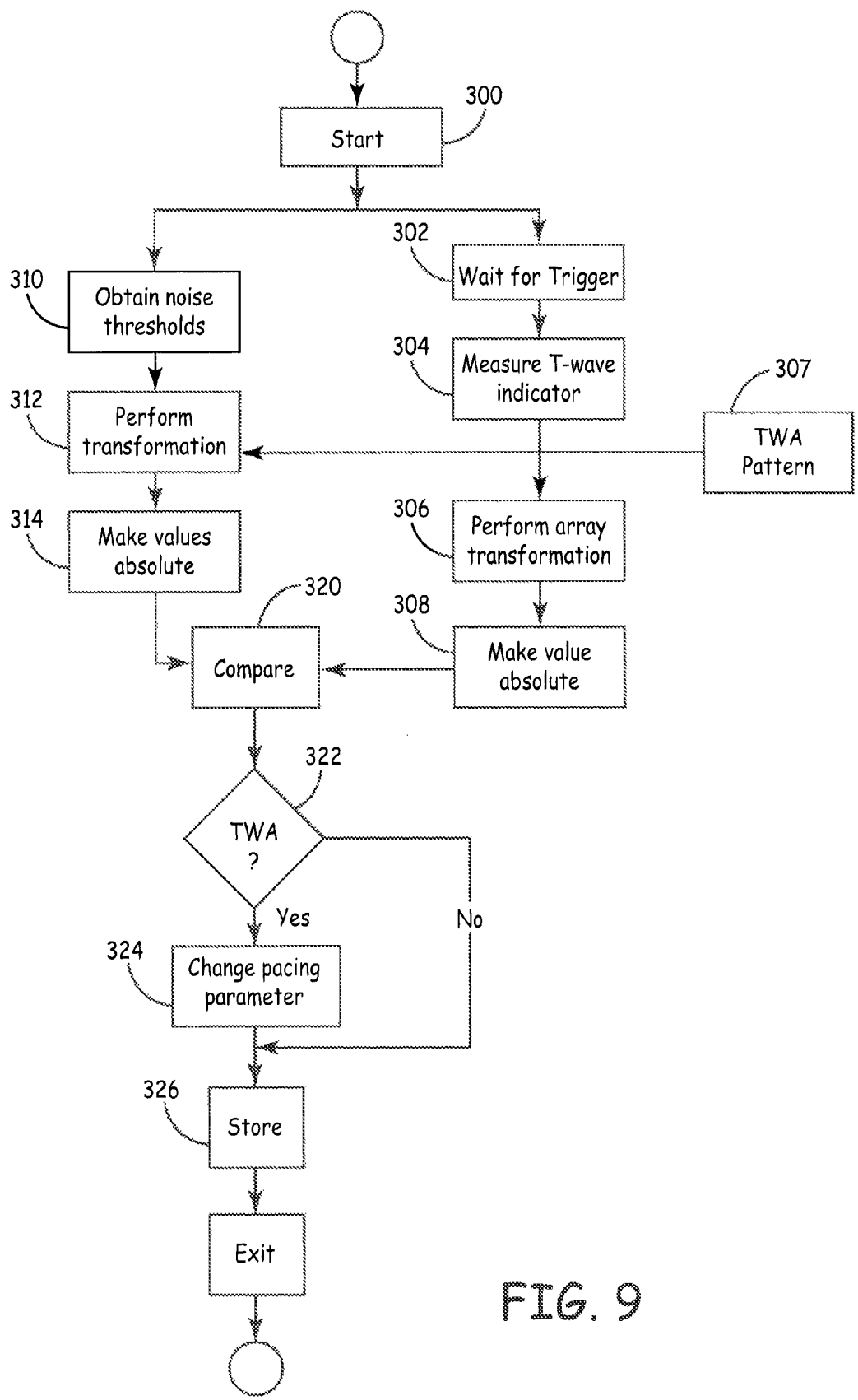
FIG. 9 is a flow diagram showing the primary steps for determining TWA in accord with this invention.

FIG. 9 represents a flow diagram showing the primary functions of a complete alternans test. The start of the test is indicated at 300 and may either be initiated from an external source by sending a programmer signal, or may be initiated automatically by an internal timer in the implanted device. Two paths are undertaken concurrently, at 302 and 310. At 302, the patient initiates exercise and the device waits for a trigger indicating that the heartbeat has been raised to an appropriate level. Alternately, the device may go into an overdrive-pacing mode and raise the patient heart rate appropriately. At 304, QT or another T-wave indicator is measured, each successive QT interval value being inputted to the array for transformation as indicated at 306, using previously recorded QT intervals. The array, or pattern is set by an input from TWA pattern memory 307, which is suitably programmable as discussed further in the connection with FIG. 10. Note that step 306 includes the high pass filter function, either by separate hardware or as part of the transformation. Each cycle the array transformation is performed at 306, and at 308 the resulting value is made absolute. At the same time, the minimal and the maximal noise thresholds are obtained at 310, transformed at 312 and made absolute at 314. The noise threshold value is inputted to the compare block 320 along with the array output, and compared. At 322 it is determined whether there is TWA. If yes, a pacing parameter, e.g. the upper pacing rate, is suitably changed as indicated at 324. Whether there is TWA or not, the result of the test is stored at 326.

Figure 10:
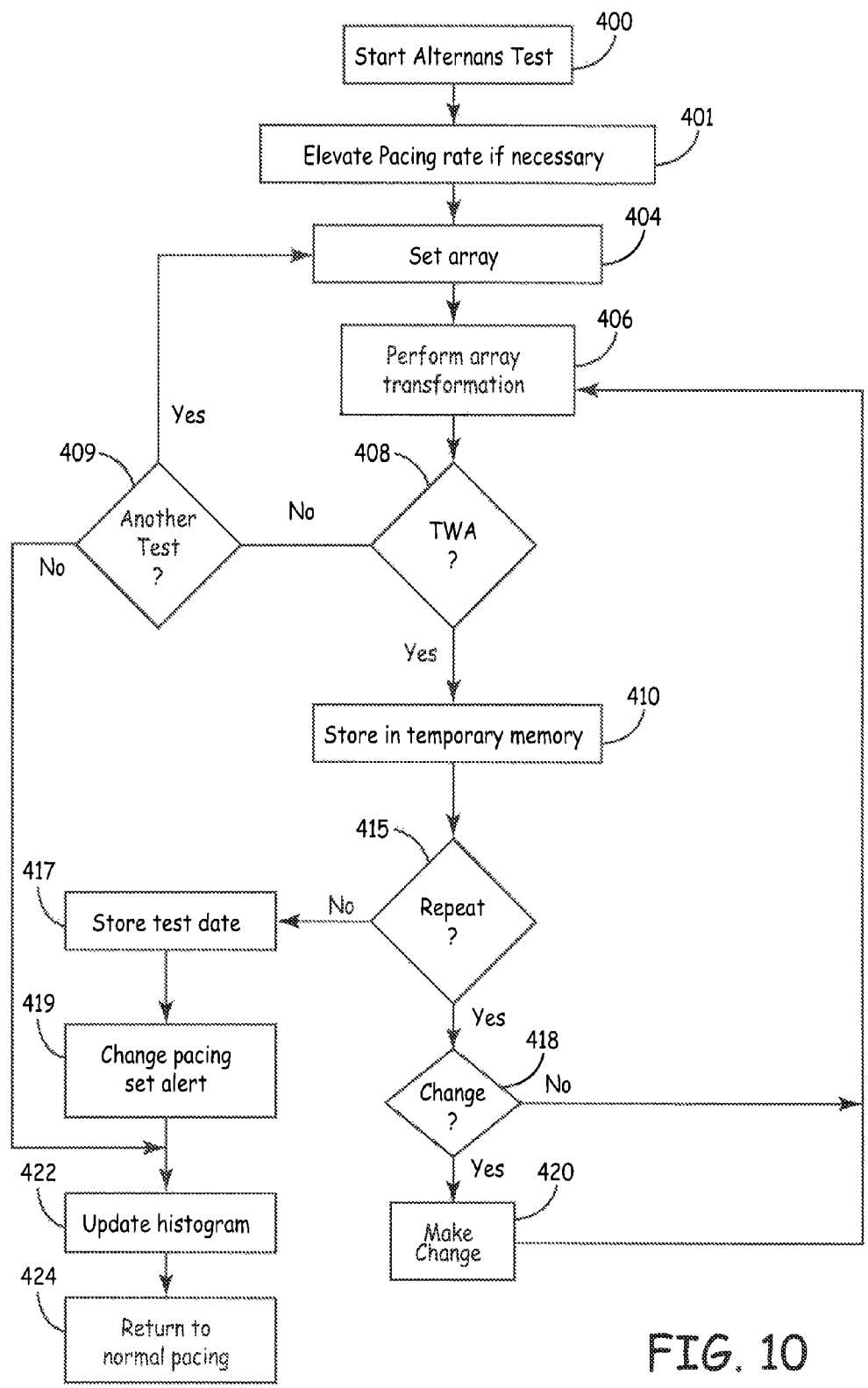
FIG. 10 is a flow diagram showing steps taken in carrying out the T-wave alternans test and in adapting the pattern array in accord with this invention.

FIG. 10 is a flow diagram showing an embodiment of the invention where multiple tests may be taken and the transformation array may be changed, either in a programmed manner or as a function of past results. The test is started at 400, and at 401 pacing rate is elevated as necessary. At 404 the array is set in accord with how the test has been programmed. In one embodiment, the array is set to a default array, which may be the last array that had been used. However, the array to be used may be programmable, and selected from arrays having different "f" and different values of n. Also, at this time an indicator may be set for later use, for indicating that at least a second test is to be performed using a second array. After n cycles, the array transformation is performed at 406 and at 408 a determination is made whether there is TWA. If no, at 409 the program determines whether another test with a different array is to be determined. This programmable feature is presented because the test may be array dependent, and it can be important to determine the types of arrays that detect TWA and those that are relatively inefficient. If yes, the new array is loaded and the program returns to 406 to do another transformation. If no, the TWA negative result is updated in a histogram as indicated at 422, and at 424 the routine is exited and the device returns to normal pacing. The histogram storage may be a histogram of alternans match levels, or of TWA/no TWA for each array. If there is TWA, this result is stored in temporary memory as indicated at 410. At 415 it is determined whether the device is programmed to repeat the task and look for successive alternans indications. If no, the test data is stored at 417, and at 419 pacing may be changed and an alert can be set. However, if at 415 the decision is to repeat the task, at 418 it is determined whether the array, or template is to be changed. This step may programmed automatically, and may suitably involve examination of the histogram data. If yes, it is changed at 420 and the routine moves back to 406 to continue array transformation based on the changed array. In this manner, a series of tests can be made, with the result of each being stored. After the series is ended, the temporarily stored data is utilized at 422 to update the histogram storage, indicating the results of the alternans tests with different arrays. This histogram data can be used subsequently to reprogram the arrays used, and for diagnostic purposes.

In an embodiment of this invention, a plurality of arrays are stored in the implanted device, for use as selected. The value of n for the arrays may be programmably selected, or automatically selected, to provide the optimum amount of flexibility and capability of determining what array or arrays work best for the patient. The arrays are preferably stored in software and the transformation is carried out by the microprocessor. However, the array memory and operation may be embodied as hardware, e.g., DSP or other equivalent digital hardware processing circuitry.

From the above, it is seen that an improved method and means of "spotting" or detecting alternans is provided. By high pass filtering and operating on differential changes each cycle, alternans is efficiently detected as soon as it exists in the patient. Further, by programming the array and keeping track of the results of alternans tests with different arrays, the most effective test for the individual patient can be determined and used.

Some of the techniques described above may be embodied as a computer-readable medium comprising instructions for a programmable processor such as microprocessor 51 or pacer timing/control circuitry 63 shown in FIG. 5, for example. The programmable processor may include one or more individual processors, which may act independently or in concert. A "computer-readable medium" includes but is not limited to any type of computer memory such as floppy disks, conventional hard disks, CR-ROMS, Flash ROMS, nonvolatile ROMS, RAM and a magnetic or optical storage medium. The medium may include instructions for causing a processor to perform any of the features described above for initiating a session of the escape rate variation according to the present invention.

The preceding specific embodiments are illustrative of the practice of the invention. It is to be understood, therefore, that other expedients known to those skilled in the art or disclosed herein, may be employed without departing from the invention or the scope of the appended claims. The present invention is not limited to any particular combination of hardware and software per se, but may find application with any form of software supplementing hardware.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures. Likewise, an implantable medical device that has elements that incorporate presently unforeseeable technology but perform the same functions within the context of the device are within the scope of the invention.

What is claimed is:

1. A method of determining an indication of T-wave alternans using an implantable medical device, comprising:
   using said device to detect time values of T-wave signals;
   storing said detected time values in a queue within said device;
operating on n of said stored time values using a transform program within said device including pattern factors in the form of alternating positive and negative factors by multiplying said stored time values by said positive and negative pattern factors to produce a value indicative of a degree of T-wave alternans;
   detecting the occurrence of T-wave alternans responsive to said indicative value exceeding a defined threshold value;
   storing a record of said occurrence of T-wave alternans within said device, and
   transmitting said record to an external device.

2. The method of claim 1, wherein the queue comprises a queue of the n most recent of said stored time values.

3. The method of claim 2, wherein said transform program comprises n alternating sign multipliers.

4. The method of claim 3, wherein operating on n of said stored time values comprises obtaining a summation of the products of multiplying said stored time values by said alternating sign multipliers.

5. The method of claim 4, further comprising converting said summation to an absolute value.

6. The method of claim 5, wherein detecting the occurrence of T-wave alternans comprises defining a noise threshold value and comparing said noise threshold value and said summation absolute value.

7. The method of claim 6, further comprising high pass filtering of said stored time values.

8. The method of claim 7, comprising using said transform array program to provide said high pass filtering of said stored time values.

* * * * *